United States Patent [19]

Baudouin et al.

[11] Patent Number: 5,545,781
[45] Date of Patent: Aug. 13, 1996

[54] PROCESS FOR DEHYDROCHLORINATING 3,4-DICHLORO-1-BUTENE TO YIELD CHLOROPRENE

[75] Inventors: Michel Baudouin, St Genis les Olliéres; Jean-Pierre Tassara, Villeurbanne, both of France

[73] Assignee: Enichem Elastomeres France S.A., Courbevoie, France

[21] Appl. No.: 308,308

[22] Filed: Sep. 19, 1994

[30] Foreign Application Priority Data

Sep. 17, 1993 [FR] France .................. 93 11302

[51] Int. Cl.$^6$ .................................. C07C 17/34
[52] U.S. Cl. .......................... 570/229; 570/219
[58] Field of Search ............... 570/216, 219, 570/229

[56] References Cited

U.S. PATENT DOCUMENTS 4,215,078  7/1980  Hargreaves, II et al. ............ 570/219

FOREIGN PATENT DOCUMENTS

| 0010672 | 5/1980 | European Pat. Off. . |
| 0010676 | 5/1980 | European Pat. Off. . |
| 0070626 | 4/1984 | Japan .................. 570/216 |
| 1173359 | 12/1969 | United Kingdom . |

*Primary Examiner*—Samuel Barts
*Attorney, Agent, or Firm*—Burns, Doane, Swecker & Mathis, L.L.P.

[57] ABSTRACT

A process for producing chloroprene by means of the dehydrochlorination of 3,4-dichloro-1-butene is disclosed, which is characterized in that the dehydrochlorination is carried out in the presence of lime and a primary amine having the general formula R—$NH_2$, in which R is a monofunctional $C_1$–$C_{15}$ hydrocarbyl radical selected from linear or branched alkyl, alkylaryl, cyclohexyl, alkylcyclohexyl, cyclopentyl, alkylcyclopentyl radicals.

13 Claims, No Drawings

PROCESS FOR DEHYDROCHLORINATING 3,4-DICHLORO-1-BUTENE TO YIELD CHLOROPRENE

The present invention relates to a process for preparing chloroprene by dehydrochlorinating 3,4-dichloro-1-butene.

It is well known that the main process for preparing chloroprene, i.e., 2-chloro-1,3-butadiene, consists in dehydrochlorinating 3,4-dichloro-1-butene (DCB) by means of sodium hydroxide. Sodium hydroxide is consumed in stoichiometric amounts and, consequently, its cost largely contributes to increase the process costs.

Therefore, the prior art tried to find out solutions which would be less burdensome than sodium hydroxide use. In particular, investigations are in course into the possibility of replacing sodium hydroxide with lime, which is cheaper. The problem which arises in this case is the low reactivity of lime.

Some DCB dehydrochlorination processes which use lime as the basic material, are disclosed in patent literature.

So, e.g., JP-51/43705 discloses a system which is constituted by sodium, calcium hydroxide and sulfate. Said process is schematically represented by the equation:

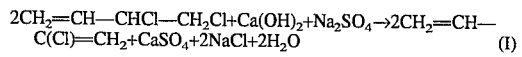

$$2CH_2=CH-CHCl-CH_2Cl+Ca(OH)_2+Na_2SO_4 \rightarrow 2CH_2=CH-C(Cl)=CH_2+CaSO_4+2NaCl+2H_2O \qquad (I)$$

The main drawback displayed by this process consists in the production of two byproducts, and namely, calcium sulfate and sodium chloride.

In particular, $CaSO_4$, which is insoluble in water, must be separated from the aqueous, sodium chloride containing solution. This operation implies self-explanatory increases in overall process costs. Furthermore, the process disclosed in that patent does not make it possible a quantitative conversion to be reached.

Other processes for DCB dehydrochlorination in the presence of ammonia or amines are reported in the literature.

FR-A-2,266,681 discloses a process of dehydrochlorination in the presence of ammonia. The selectivity to CP is high, but the conversion rate is rather poor. The process requires the presence of such a polar solvent as N,N-dimethylformamide and, furthermore, a recycle of ammonia is not provided for.

JP-A-51/54504 discloses a process which makes it possible satisfactory selectivity values to be reached, but which requires that ethylene diamine is used as the dehydrochlorinating agent. However, also in this case, a recycle of ethylene diamine is not contemplated.

This being the present state of the art, the present Applicant has now developed a process for dehydrochlorinating DCB to yield chloroprene, which process overcomes the above cited drawbacks.

In accordance with the above, the present invention relates to a process for producing chloroprene by means of the dehydrochlorination of 3,4-dichloro-1-butene which process is characterized in that the dehydrochlorination is carried out in the presence of lime and a primary amine having the general formula $R-NH_2$, in which R is a monofunctional $C_1-C_{15}$ hydrocarbyl radical selected from linear or branched alkyl, alkylaryl, cyclohexyl, alkylcyclohexyl, cyclopentyl, alkylcyclopentyl radicals.

The process according to the present invention takes place according to the following equation:

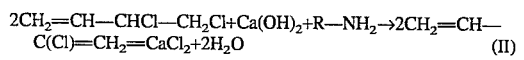

$$2CH_2=CH-CHCl-CH_2Cl+Ca(OH)_2+R-NH_2 \rightarrow 2CH_2=CH-C(Cl)=CH_2=CaCl_2+2H_2O \qquad (II)$$

By the term "lime", as used herein, calcium oxide, calcium hydroxide or their mixtures are meant.

Advantageously, the radical R is selected from linear or branched-chain $C_1-C_6$, preferably $C_3-C_4$ alkyl and cycloalkyl radicals and, still more preferably, is an n-butyl or isopropyl radical. According to the present invention, one amine, or a mixture of a plurality of amines, can be used.

According to an embodiment, the process according to the present invention is carried out according to a single-step procedure, i.e., causing DCB, lime and the amine to react simultaneously.

According to a preferred embodiment, the process according to the present invention comprises the following steps, carried out sequentially:

(a) dehydrochlorination of 3,4-dichloro-1-butene in the presence of the primary amine $R-NH_2$, to yield chloroprene and $R-NH_2.HCl$;

(b) treatment of $R-NH_2.HCl$ with lime in order to liberate and subsequently recover $R-NH_2$.

The only difference between the single-step and the double-step processes consists in the dehydrochlorination, which is carried out, in the first case, in the presence of lime and amine and, in the second case, with amine only, with lime being added to the reaction mixture after the dehydrochlorination reaction and recovery of chloroprene (CP).

The dehydrochlorination, whether in the presence of amine and lime, or in the presence of amine only, is advantageously carried out at a temperature comprised within the range of from 20° to 120° C., preferably of from 30° to 70° C. The above step can be carried out, if so required, in the presence of an inert solvent, e.g., a hydrocarbonaceous solvent. However, for self-explanatory economic reasons, it should preferably be carried out without any solvents.

Advantageously, as solvent an excess of $R-NH_2$ can be used. As a consequence, the molar ratio of $R-NH_2$ to DCB is of at least 1:1; however, the use of an amine excess is preferably used, which should be preferably of from 1.5 to 6 mol of amine per each mol of DCB.

In the case of the dehydrochlorination in the presence of amine and lime, the molar ratio of DCB:amine:lime is comprised within the range of from 1:1:0.5 to 1:6:1.5, preferably of from 1:1.5:0.6 to 1:4:1.

The dehydrochlorination can be allowed to proceed until an either partial or nearly total conversion of DCB to yield CP, is obtained. However, the conversion of DCB into CP should be caused to proceed as far as possible, in order to reduce the separation and recycle problems.

As regards the necessary time for the dehydrochlorination, said time is a function of the desired conversion rate and of the selected temperature. For exemplifying purposes, for a complete conversion of DCB at a temperature of 60° C., the dehydrochlorination duration is of approximately 160–200 minutes.

When the dehydrochlorination has come to an end, chloroprene is recovered by means of conventional techniques, such as extraction or distillation. However, it is preferable that the distillation of the reaction mixture coming from the hydrochlorination is carried out.

In such a way, produced chloroprene is recovered with, in the case when the amine has a not too high boiling temperature, at least one portion of the possibly used amine excess being recovered as well.

The optimal distillation conditions (column type and packing, reflux rate, and so forth) are selected as a function of the difference between chloroprene and amine boiling temperatures. When the boiling point of the amine so allows, the distillation should be preferably carried out under atmospheric pressure. Due to this reason, and as it was already stated herein, n-butylamine and isopropylamine are preferred. Under the atmospheric pressure, n-butylamine has a boiling point of 78° C., and isopropylamine of 35° C., whilst CP boils at 59° C. It derives from these values that in the first case CP will be collected before, as the overhead fraction, whilst when isopropylamine is used, this is the compound which will be collected first. After CP separation, the residual amine is recovered by distillation or extraction.

During DCB dehydrochlorination and amine recovery, it is recommended to operate in the presence of a polymerization inhibitor agent, well known to those skilled in the art, such as, e.g., phenothiazine and tert.-butyl catechol. In that way, the amount of byproduct of polymeric nature is reduced. Furthermore, all the operations implied by the present process should be preferably carried out in the presence of an inert gas, e.g., nitrogen.

In the case of the two-step reaction and after CP recovery, the residue from the (a) step, containing $RNH_2 \cdot HCl$ and a portion of the possibly present excess of $RNH_2$, is submitted, in the (b) step, to the treatment with lime in order to liberate the amine from its hydrochloride salt according to the following scheme (shown, for exemplifying purposes, for CaO):

$$CaO + 2RNH_2 \cdot HCl \rightarrow CaCl_2 + 2RNH_2 + H_2O.$$

As a consequence, the amount of CaO or $Ca(OH)_2$ should be of at least 0.5 mol of calcium per each hydrochloride mol. However, it is suggested that at least a small excess of lime should be used, with the reaction being fed with, preferably, from 0.52 mol to 1 mol of calcium per each mol of hydrochloride.

In order to facilitate the contact between lime and hydrochloride and removing the heat developed by the reaction (the reaction of both species with each other is an exothermic and fast one), it is advisable to dilute the system with water. The optimal water amount is selected as a function of the technique which will be subsequently selected in order to recover the amine (extraction or distillation). In general, a water amount is sufficient which is from 3 to 6 times as large than the amount of lime, by weight.

After collecting CP and liberating the amine from its hydrochloride, the recovery of the same amine carried out according to traditional techniques, in particular by extraction or distillation.

The extraction will be applied in those cases when the amine has a high boiling temperature and not too much soluble in water; in that case, a larger water amount can be used.

Inasmuch as according to the preferred embodiment, the process according to the present invention uses $C_1$–$C_6$ amines (all having, with the exception of $C_5$–$C_6$ amines, lower boiling temperatures than water) using the distillation technique recommended. In such a case, for the dilution a water amount will be used which is as small as possible. The distillation parameters will be selected as a function of the amine boiling point and, in particular, of the difference of its boiling temperature from water.

The distillation residue is essentially constituted by calcium chloride, a possibly present calcium excess, and water. It can sometimes contain traces of heavy product deriving from DCB and amine decomposition. In this case, an end extraction should be carried out with small amounts of an organic solvent, which can be mixed with water, in order to extract said byproducts.

The so recovered amine can be used for subsequent cycles of DCB dehydrochlorination.

Furthermore, in the case of the two-step reaction, the process can be carried out inside one single reactor ("one-pot process"), which, in that case, should allow the reactants to be refluxed during the step (a) with the distillation column being excluded.

The following examples are reported in order to illustrate the present invention in greater detail.

EXAMPLE 1

Dehydrochlorination of DCB with n-butylamine.

The reaction equipment is constituted by a glass flask of 500 cm$^3$ equipped with mechanical stirring means and heated with an oil bath. The flask is also equipped with an overhanging distillation column equipped with a 30 cm-high stainless steel Multiknit device, and with an addition funnel of 100 cm$^3$.

The flask is charged with 62.5 g of DCB, i.e., 3,4-dichlorobutene-1 (0.5 mol) and 146 g of n-butylamine (2 mol).

n-Butylamine is charged to the flask and the whole equipment is kept at 60° C., with stirring.

DCB is added to the amine during 30 minutes, with, during said time interval, the temperature being always kept at 60° C. After the addition, the reaction is allowed to proceed for further 195 minutes at 60° C.

The reaction mixture is subsequently heated and distilled with a reflux rate, at column head, of about 20:1.

Three fractions are distilled according to as displayed in Table 1. The three distilled fractions, and the residue which remains in the kettle, are all analyzed by gas chromatography in order to determine their contents in chloroprene and DCB.

TABLE 1

| Fraction No. | Kettle temperature (°C.) | Head temperature (°C.) | Time (minutes) | Fraction weight | CP content |
|---|---|---|---|---|---|
| 1 | 76–80 | 57,2–58,2 | 60 | 27,2 g | 97,9% |
| 2 | 80–84 | 57,8–70 | 35 | 17,3 g | 68,4% |
| 3 | 84–88 | 70–73 | 40 | 25,8 g | 13,9% |
| Kettle residue | | | | 136,6 g | 0,2% |

The balance of the operation displays that DCB has totally been converted and 42.3 g of chloroprene (CP) were formed. The reaction yield, based on charged DCB, is 95.6%.

EXAMPLE 2

Recovery of n-butylamine by starting from its hydrochloride, by reaction with lime and distillation.

146 g (2 mol) of n-butylamine, 36 g (0.99 mol) of HCl and 64 g of water are charged to the apparatus disclosed in Example 1.

In such a way, a reaction mixture is obtained which consists of n-butylamine hydrochloride, free amine and water. To this mixture, 33.6 g (0.60 mol) of CaO is added.

The temperature increases from 20° C. to 46° C. The reaction is allowed to proceed for 1 hour with stirring. The mixture is then heated and distilled under atmospheric pressure, with a reflux rate of 10.

Three distilled fractions in sequence and a residue in the kettle are obtained.

The distilled fractions (Table 2) are analyzed by means of a potentiometer in order to determine the butylamine (But.) percent contents thereof. The residue in the kettle is analyzed in order to determine the total percent content of elemental carbon thereof.

TABLE 2

| Fraction No. | Kettle temperature (°C.) | Head temperature (°C.) | Fraction weight | But. assay |
| --- | --- | --- | --- | --- |
| 1 | 89–94 | 73–76 | 72,8 g | 96,8% |
| 2 | 94–102 | 73–69 | 61,1 g | 97,1% |
| 3 | 109–117 | 70–73 | 7,3 g | 97,3% |
| Kettle residue | | | 121,2 g | C:4240 mg/kg |

The material balance shows that in the distilled material 136.9 g of n-butylamine was recovered, i.e., the recovery yield was of 93.8%.

The percent content of total elemental carbon in the residue shows that this fraction cannot contain more than 0.78 g of n-butylamine, i.e., 0.5% of used amine.

In such a way, it was shown that during the course of the regeneration of the amine by treating its hydrochloride salt with lime, the regenerated amine can be separated from produced $CaCl_2$, by distillation.

EXAMPLE 3

By operating according to the same procedure as disclosed in Example 1, further tests were carried out by using different primary amines (butylamine and cyclohexylamine) and, within the limits of DCB dehydrochlorination step, under different experimental conditions.

The results are reported in Table 3. In this Table, in the third, last-but-one and last columns, the molar ratio of amine:DCB, the overall conversion of DCB and the selectivity to CP are reported, respectively.

In Example 4, DCB was fed to the amine containing reactor which already contained the amine.

TABLE 3

| Example No. | Amine | Amine: DCB | Temp. (°C.) | Time (Minutes) | Total DCB conversion | Selectivity to CP |
| --- | --- | --- | --- | --- | --- | --- |
| 3 | But. | 1,9 | 40–56 | 180 + 120 | 94% | 97% |
| 4 | But. | 1,9 | 40 | 320 | 89% | 69% |
| 5 | Cyclo. | 1,9 | 40 | 180 | 41% | 98% |
| 6 | But. | 1,8 | 40 | 170 | 81% | 100% |
| 7 | But. | 1,8 | 60 | 120 | 94% | 100% |
| 8 | But. | 1,8 | 60 | 140 | 94% | 100% |

EXAMPLE 4

In this Example, a complete process of dehydrochlorination with recycle of the amine used in the dehydrochlorination, is disclosed. All process steps are carried out under a nitrogen blanketing atmosphere.

To a reactor of 250 ml, 146 g (2 mol) of n-butylamine and 0.2 g of phenothiazine are charged.

The reaction mixture is heated up to about 60° C., then 62.5 g (0.5 mol) of DCB is added to the reactor during 30 minutes.

The reaction is allowed to proceed during 150 minutes at 60° C., with CP being caused to reflux into the flask.

Three fractions of chloroprene (F1, F2, F3) are then distilled, and the residue is allowed to cool. The recovery inside the traps is of 3 g.

An amount of 17 g of CaO (0.30 mol) and 32 g of water are added; the temperature increases from 40° to 55° C. and is allowed to remain that value during 60 minutes.

An amount of 47 g of water is then added and the bottom is heated up to 110° C.; 74 g is distilled (F4).

When cold, 90 g of cyclohexane, then 15 g of water and 25 g of cyclohexane, for washing purposes, are added.

By decantation, 113.5 g (F5) of organic phase and 149.2 g (F6) of aqueous phase are separated.

The composition of each fraction is summarized in Table 4, in which DCB percent levels were not reported, because they were always lower than the analytical detection threshold value.

TABLE 4

| | | CP | | n-butylamine | |
| --- | --- | --- | --- | --- | --- |
| Reference | Weight (g) | % | g | % | g |
| F1 | 12,1 | 95,7 | 11,6 | 4,3 | 0,5 |
| F2 | 60,6 | 33,4 | 20,2 | 66,6 | 40,4 |
| F3 | 22,2 | 33,1 | 7,4 | 66,9 | 14,8 |
| Traps | 3,0 | 100 | 3,0 | — | — |
| F4 | 74,0 | — | — | 100 | 74,0 |
| F5 | 113,5 | — | — | 1,8 | 2,0 |
| F6 | 149,2 | — | — | 6,6 | 9,8 |
| Total | | | 42,2 | | 140,5 |

The operation balance shows that dichlorobutene was totally trasformed, with 42.2 g (0.48 mol) of chloroprene being obtained, and that 140.5 g of n-butylamine was recovered, i.e., the recovery yield was of 96.2%.

EXAMPLE 5

The process is carried out according to the same procedure as disclosed in Example 4, but with butylamine being replaced with isopropylamine.

Operating conditions: molar ratio of isopropylamine:DCB=4; dehydrochlorination temperature: 60° C.; dehydrochlorination duration: 180 minutes; overpressure: 1.6 bars.

| Results: | |
| --- | --- |
| DCB conversion: | 99.75%; |
| Selectivity to CP: | 96.5%; |
| Amine recovery: | 95.3%. |

EXAMPLE 6

The process is carried out according to the same procedure as disclosed in Example 4, but with butylamine being replaced by hexylamine.

Operating conditions: molar ratio of hexylamine:DCB=4; dehydrochlorination temperature: 60° C.; dehydrochlorination duration: 180 minutes.

| Results: | |
| --- | --- |
| DCB conversion: | 99.8%; |
| Selectivity to CP: | 63%. |

EXAMPLE 7

4 Mol of isopropylamine (236 g), phenothiazine (400 mg) and 0.55 mol of lime (CaO) (30.8 g) are charged to a reactor.

The reaction media is brought to 60° C. and during the course of 45 minutes 1 mol (125 g) of DCB is added. The temperature is kept at 60° C. for 3 hours, up to approximately the addition end.

When the reaction is ended, the temperature is decreased down to 24° C. and 200 g of water is added.

The reaction media is distilled; the following fractions are obtained:

a head fraction containing:
 83.2 g of chloroprene;
 228.5 g of isopropylamine;
 0.5 g of unreacted DCB;

the distillation bottom contains water, calcium chloride, lime [Ca(OH)$_2$] and 9.8 g of "heavy products".

| | |
|---|---|
| DCB conversion | 99.6%. |
| Selectivity to CP | 94%. |
| Amine recovery = | 96.8%. |

COMPARISON EXAMPLE 8

The process is carried out according to the same procedure as disclosed in Example 4, but with butylamine being replaced with aniline.

Operating conditions: molar ratio of aniline: DCB=4; dehydrochlorination temperature: 60° C.; dehydrochlorination duration: 180 minutes.

| Results: | |
|---|---|
| DCB conversion: | 38.8%; |
| Selectivity to CP: | 0.2%. |

We claim:

1. A process for producing chloroprene by dehydrochlorination of 3,4-dichloro-1-butene (DCB) comprising conducting the dehydrochlorination reaction in the presence of lime and a primary amine having the formula R—NH$_2$, in which R is a monofunctional C$_1$–C$_{15}$ hydrocarbyl radical selected from the group consisting of linear or branched alkyl, alkylaryl, cyclohexyl, alkylcyclohexyl, cyclopentyl, and alkylcyclopentyl radicals.

2. A process for preparing chloroprene by dehydrochlorination of 3,4-dichloro-1-butene, (DCB) comprising:
 (a) dehydrochlorination of 3,4-dichloro-1-butene in the presence of a primary amine R—NH$_2$, to produce chloroprene and R—NH$_2$.HCl; and
 (b) treatment of said R—NH$_2$.HCl with lime to produce R—NH$_2$.

3. The process according to claim 1 or 2, wherein the radical R contained in the primary amine R—NH$_2$ is selected from the group consisting of linear or branched-chain C$_1$–C$_6$ alkyl and cycloalkyl radicals.

4. The process according to claim 3, wherein the radical R contained in the primary amine R—NH$_2$ is selected from the group consisting of linear and branched-chain C$_3$–C$_4$ alkyl radicals.

5. The process according to claim 4, wherein R is selected from the group consisting of n-butyl and isopropyl radicals.

6. The process according to claim 1 or 2, wherein the dehydrochlorination reaction is carried out at a temperature ranging from 20° to 120° C.

7. The process according to claim 6, wherein the dehydrochlorination reaction is carried out at a temperature ranging from 30° to 70° C.

8. The process according to claim 1, wherein the molar ratio of 3,4-dichloro-1-butene, amine and lime ranges from 1:1:05 to 1:6:1.5.

9. The process according to claim 1, wherein the molar ratio of 3,4-dichloro-1-butene, amine and lime ranges from 1:1.5:0.6 to 1:4:1.

10. The process according to claim 2, wherein in the dehydrochlorination step (a), the molar ratio of R—NH$_2$:DCB is at least 1:1.

11. The process according to claim 10, wherein in the dehydrochlorination step (a), the molar ratio of R—NH$_2$:DCB ranges from 1.5 to 6 mole of amine per moles of DCB.

12. The process according to claim 2, wherein in step (b), the molar ratio of lime:R—NH$_2$.HCl is at least 0.5:1.

13. The process according to claim 12, wherein in step (b), the molar ratio of lime:R—NH$_2$.HCl ranges from 0.52 to 1 mole of lime per each mole of R—NH$_2$.HCl.

* * * * *